US008675192B2

(12) United States Patent
Ugolin et al.

(10) Patent No.: US 8,675,192 B2
(45) Date of Patent: Mar. 18, 2014

(54) METHOD AND DEVICE FOR HIGH SPEED QUANTITATIVE MEASUREMENT OF BIOMOLECULAR TARGETS ON OR IN BIOLOGICAL ANALYSIS MEDIUM

(75) Inventors: Nicolas Ugolin, Paris (FR); Denis Menut, Creteil (FR); Julien Le Meur, Pont-Aven (FR); Nadine Coulon, Dourdan (FR); Sylvie Chevillard, Le Kremlin-Bicetre (FR); Emilie Bosc, Fontenay-aux-Roses (FR); Jean-Marc Joseph Desaulniers, Binic (FR)

(73) Assignee: Commissariat a l'Energie Atomique et Aux Energies Alternatives, Paris (FR)

( * ) Notice: Subject to any disclaimer, the term of this patent is extended or adjusted under 35 U.S.C. 154(b) by 600 days.

(21) Appl. No.: 12/933,350

(22) PCT Filed: Mar. 20, 2009

(86) PCT No.: PCT/FR2009/000300
§ 371 (c)(1),
(2), (4) Date: Jan. 6, 2011

(87) PCT Pub. No.: WO2009/122047
PCT Pub. Date: Oct. 8, 2009

(65) Prior Publication Data
US 2011/0109904 A1  May 12, 2011

(30) Foreign Application Priority Data
Mar. 20, 2008 (FR) ..................... 08 01534

(51) Int. Cl.
*G01J 3/30* (2006.01)
(52) U.S. Cl.
USPC .......................................... 356/318
(58) Field of Classification Search
CPC ................................... G01N 21/718
USPC ........................... 356/313, 316, 318
See application file for complete search history.

(56) References Cited

U.S. PATENT DOCUMENTS 4,526,690 A * 7/1985 Kiovsky et al. ............... 210/335
5,781,289 A   7/1998 Sabsabi et al.
(Continued)

FOREIGN PATENT DOCUMENTS

DE  43 41 462    6/1995
JP  1-321340    12/1989
(Continued)

OTHER PUBLICATIONS

Le Meur, et al., "First Improvements in the Detection and Quantification of Label-Free Nucleic Acids . . . ", Spectrochimica Acta Part B, 63, pp. 465-473, 2008.

*Primary Examiner* — Kara E Geisel
*Assistant Examiner* — Shawn Decenzo
(74) *Attorney, Agent, or Firm* — Morgan, Lewis & Bockisu LLP

(57) ABSTRACT

The present invention relates to a device and method for the high speed quantitative measurement of biomolecular targets on the surface or in the body of a planar medium for biological analysis. The method, according to the invention, includes the following, steps: a) at least two laser beams (F") are focused and overlaid on each measuring point of said medium by the simultaneous intersection of these beams to extract a contained hot plasma (P), including a measured chemical element present in the targets and another chemical element exogenous to the targets and present in a known quantity on this medium; b) luminous emission rays for each plasma, corresponding to the quantified element and exogenous element, are detected and analyzed for each measuring point while measuring the brightness of these rays; then c) the concentration in each measuring point of the quantified element is determined through prior calibration of the rays of the qualified element to determine a correlation between the brightness of the rays, specific to said element, and the concentrations of the latter in mixtures of the quantified element and exogenous element in known proportions.

40 Claims, 4 Drawing Sheets

(56) References Cited

U.S. PATENT DOCUMENTS

| | | | |
|---|---|---|---|
| 6,008,897 A * | 12/1999 | Sabsabi et al. | 356/318 |
| 6,287,776 B1 * | 9/2001 | Hefti | 435/6.11 |
| 6,463,314 B1 | 10/2002 | Haruna | |
| 6,661,511 B2 * | 12/2003 | Detalle et al. | 356/318 |
| 6,700,660 B2 * | 3/2004 | Sabsabi et al. | 356/318 |
| 7,599,048 B2 * | 10/2009 | Yoo et al. | 356/72 |
| 7,663,749 B2 * | 2/2010 | Levesque et al. | 356/318 |
| 8,093,030 B2 * | 1/2012 | Schoenfeld et al. | 435/194 |
| 2003/0215872 A1 * | 11/2003 | Clark | 435/7.1 |
| 2004/0189990 A1 * | 9/2004 | Shilling | 356/318 |
| 2005/0084980 A1 * | 4/2005 | Koo et al. | 436/171 |
| 2007/0076200 A1 | 4/2007 | Martin et al. | |
| 2007/0279628 A1 * | 12/2007 | Lipson | 356/317 |
| 2010/0277718 A1 * | 11/2010 | Zhang et al. | 356/51 |

FOREIGN PATENT DOCUMENTS

| | | |
|---|---|---|
| JP | 2007-3510 | 1/2007 |
| WO | WO 00/20847 | 4/2000 |
| WO | WO 2008/034968 | 3/2008 |

* cited by examiner

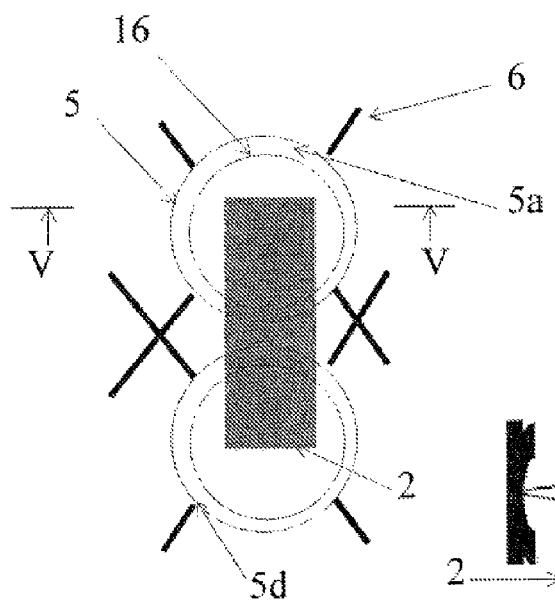
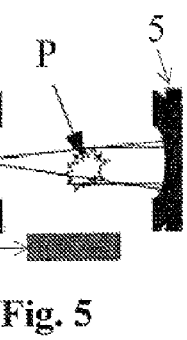
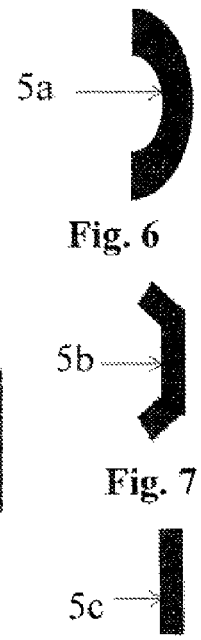
Fig. 4        Fig. 5        Fig. 6
Fig. 7
Fig. 8
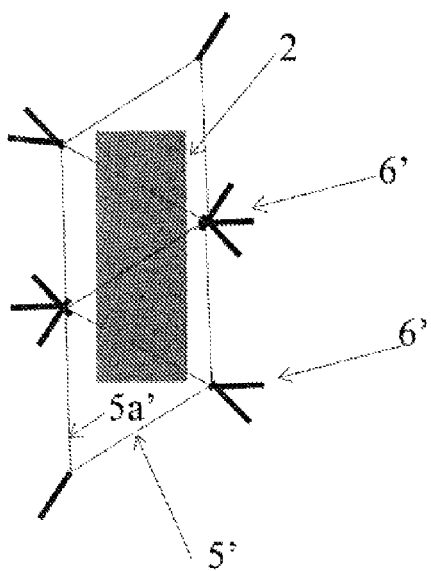
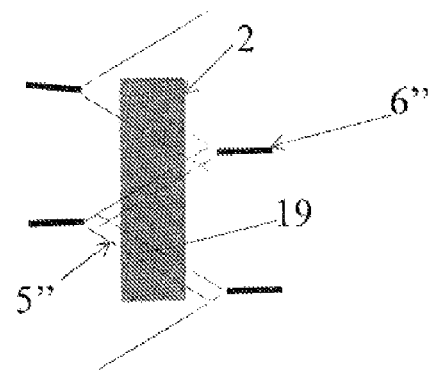
Fig. 9        Fig. 10

METHOD AND DEVICE FOR HIGH SPEED QUANTITATIVE MEASUREMENT OF BIOMOLECULAR TARGETS ON OR IN BIOLOGICAL ANALYSIS MEDIUM

RELATED APPLICATIONS

The present application is a U.S. National Phase Application of International Application No. PCT/FR2009/000300 (filed Mar. 20, 2009) which claims priority to French patent application Ser. No. 08/01534 (filed Mar. 20, 2008) which are hereby incorporated by reference in their entirety.

FIELD OF THE INVENTION

The present invention relates to a method for the high speed quantitative measurement of biomolecular targets at the surface or in the body of a planar biological analysis support, and a device for implementing this method. The invention applies in particular to the quantitative measurement of unlabeled nucleic acids or proteins segregated at the surface or in the body of a preferably planar biological analysis support, such as a biochip for example comprising an array of probes, a transfer membrane, an electrophoresis or chromatography gel, or a support made of glass or of polyimide (e.g. made of Kapton®), in a nonlimiting manner.

BACKGROUND

The laser-induced breakdown spectroscopy (LIBS) technique is a very powerful method for determining the elemental composition of the surface of a material. This composition is obtained by measuring the emission lines coming from the atoms or the ions constituting a transient plasma induced at the surface of the material by a laser beam, and the elemental analysis of this surface can be obtained by scanning said surface by means of a laser source performing successive shots according to a regular grid, so as to map the surface of this material. At each laser shot, the emission spectrum of the chemical elements being investigated is recorded, as are the coordinates for focusing of the beam at the surface of the material. It is then possible to reconstitute a point-by-point image of the surface of the material at a selected wavelength corresponding to a given chemical element. If a calibration method is applied, the variations in intensity of the image obtained by mapping indicate the abundance of this element at the surface of the material.

However, a major drawback of this technique is that the very high number necessary for carrying out a high-resolution mapping of the surface (resolution of between 300 nm and 1 μm) implies analysis times of several hours or even several days, as soon as the surface area analyzed exceeds a few square millimeters. This slowness of the image acquisition makes LIBS inapplicable as a method of analysis for a large number of applications in biology, and more particularly for genomics and proteomics.

In the genomics field, biochips represent a major revolution in the molecular biology techniques of the past ten years. By enabling the simultaneous study of the level of expression of several hundred, or even several thousand, genes, they make it possible to grasp the impact of a disease or of a stress (e.g. resulting from radiation, from pollution or from taking a medicament) at the level of the complete genome of an individual. These techniques are thus becoming increasingly used in modern biology.

Biochips are divided up into two major families, comprising microfluidic chips and probe-array chips. The latter are organized in arrays of "spots" or measuring points, and they are generally obtained by depositing or synthesizing, at precise coordinates on a passive support, molecular probes formed from biopolymers such as DNA, proteins or antibodies, for example. These probe-array biochips make it possible to identify the targets present in a biological sample when these targets hybridize specifically at each "spot" of probes.

There are, on the one hand, high-complexity biochips (more than 5000 spots) for pan-genomic studies and, on the other hand, low-complexity and medium-complexity biochips, which are dedicated to a given purpose (e.g. therapeutic tests, biological detector).

The current probe-array biochip technology has a certain number of major limitations, in particular:
  the high steric hindrance of fluorescent labels, which sporadically modify the recognition between probes and targets and thus leads to numerous measurement artefacts, decreasing the reproducibility of the experiments;
  the absence of quantitative measurement, which prohibits comparison of the levels of expression between two different targets; and
  the high cost of this current technology, both in terms of production and in terms of implementation.

It is the reason why several alternatives to this technology have recently been developed, with in particular:
  "RT-PCR" technologies in microfluidic cards ("Reverse Transcriptase Polymerase Chain Reaction", i.e. chain amplification by polymerase after reverse transcription of a ribonucleic acid into complementary DNA), which make it possible to amplify up to 386 different targets in parallel, with simplification of the implementation and improved detection, which are, however, penalized by the absence of quantitative measurement for a real comparison between targets, by the limitation of the number of targets to be analyzed (much lower than a low-complexity biochip) and by a high implementation cost;
  biochips on "Nylon" film, based on the hybridization of targets in a large volume and chemiluminescence labeling, which also provide simplified implementation and improved detection, but which are nevertheless penalized by the absence of quantitative measurement, the large reaction volume required (which is limiting for analyzing samples of low concentration) and the very high production and implementation costs; and
  new concepts of biochips without labeling, which are based on the detection of the target by measuring impedence or by surface plasmon resonance (SPR), and which have in particular been described in David F et al., Bioscience Bioelectron. 2005, in Li C. M. et al., Front Biosci. 2005 or in Macanovic A. et al., Nucleic Acid Research 2004, but which do not make it possible to quantify the number of targets, pose a problem for preparing high-density chips and involve, both for the impedence measurement technique and for the SPR technique, measurement artefacts due to the varying sizes and conformations of the targets.

ICP (inductively coupled plasma) spectrometry methods have also been developed, cf. Inchul Yang et al., Analytical Biochemistry (2004), vol. 335, 150-161 or Heinrich F. Arlinghaus et al., Analytical Chemistry (1997), vol. 69, No. 18, 3747-3753, said methods making it possible to assay the phosphorus contained in a nucleic acid in order to estimate, for example, the degree of hybridization thereof to a PNA (peptide nucleic acid) biochip.

However, it appears that the use of mass spectrometry for assaying phosphorus using a plasma generated at the surface of a biochip is a slow method (typically taking several hours per cm² on the biochip), and that the instrumentation necessary for implementing it is expensive. In addition, it should be noted that this ICP spectrometry technique is not quantitative, since it provides only the crude quantity of nucleotides hybridized, without being able to differentiate between the size and the number of the biomolecules.

Patent document US-A-2006/0105354 presents a method of real-time quantification of multiple targets formed from labeled nucleic acids and which are bound to the surface of a probe-array biochip, comprising, in particular, emission of an excitation laser beam at the surface of the array and measurement of the light emission from the hybridized targets in response to this excitation beam.

A major drawback of this method is that it also is not quantitative within the meaning indicated above, and it requires, in addition, the presence of labeled molecules bound to the target molecules.

In the proteomics field, the problem which arises is even more complicated. This is because, in addition to identifying, in a cell extract, the proteins present and also their concentrations, it is necessary to identify their post-translational modifications. This is because the activity of a protein is very often determined by its post-translational modifications. Among the possible modifications, phosphorylations are without doubt the most biologically significant.

Two-dimensional (2D) electrophoresis techniques are the parallel analysis techniques most commonly used for analyzing mixtures of proteins. These techniques consist in migrating a mixture of proteins in a gel, successively in two orthogonal directions, as a function of different physicochemical criteria (e.g. chromatography or electrophoresis). The proteins are then separated according to their affinity with respect to a solvent, their electric charge, their mass, their shape, their modification, etc., and, after having been pigmented with an optionally fluorescent pigment, the proteins are identified according to their position or spot on the 2D gels relative to migrations obtained in a reference gel. To demonstrate the post-translational modifications, in particular phosphorylations, it is necessary to analyze each spot of the gel. Various methods of analysis are possible, such as mass spectrometry, NMR, immunological labeling or the ICP technique, for example.

The demonstration of post-translational modifications is for the moment very laborious to carry out.

For a few years, antibody biochips have been available on the market for analyzing protein extracts. These biochips make it possible to analyze, in parallel, the expression of several hundred genes in their protein form, provided that antibodies specific for the desired proteins exist. However, this technology is limited by the need to label the proteins. Unfortunately, the chromophores used for the labeling randomly modify the affinity of the proteins for their antibody. Furthermore, since the labeling is also random, the results are difficult to interpret and difficult to compare between various experiments. In order to evaluate, by this technique, for example, the degree of post-translational modifications of a given protein between two conditions or two cell types, it is necessary to have two antibodies which exclusively recognize each of the forms of the protein. In addition to being expensive, this is technically very difficult to obtain.

The LIBS technique represents an alternative for the analysis, without prior labeling, of biomolecules segregated on all types of supports (e.g. membrane, gel, plastic support, for example Kapton® support, silicon support), these supports being the main types used in biological analyses. The method for analyzing a biological product by LIBS consists in assaying a chemical element constituting the target biomolecule previously isolated, segregated or purified on a chromatography support, an electrophoresis support, a membrane or a biochip.

As indicated above, the main technological bottleneck of an analysis by LIBS is the slowness of the method, which greatly limits the use of this technique in biology. This is because analysis supports in biology often have a surface area of several square centimeters. The imaging, at a resolution of 10 microns for example, of a 1 cm² analysis support thus requires 1 000 000 contiguous laser shots to be carried out, at a rate of one shot per position. Of course, this number has to be multiplied by the number of shots to be carried out per position, if the molecule to be analyzed is in the body of the support, as occurs for electrophoresis gels, for example.

In order to carry out this analysis in 1 second, it is necessary to have a mega Hertz UV laser with sufficient energy to induce a plasma on the support at each shot (energy typically greater than 60 microjoules per pulse). In order to carry out this analysis in 1 minute, it is necessary to have a UV laser with a frequency equal to 600 kilo Hertz and sufficient energy to induce a plasma on the support at each shot (also greater than 60 microjoules per pulse). This problem can be minimized by carrying out noncontiguous shots, in return for a degradation in resolution. However, the frequency remains high, even for a very degraded image.

It is possible to use lasers with longer wavelengths, for example around 532 nm, owing to the fact that these lasers generally have higher frequencies and higher energies. However, when moving away from the far UV (266 nm), the energy required to obtain an analyzable plasma increases and, for example, lasers at 532 nm—of sufficient energy—have frequencies in the vicinity of far UV lasers, which then poses the same problem as for the far UV range.

BRIEF SUMMARY OF THE INVENTION

An objective of the present invention is to propose a method for the high speed quantitative measurement of biomolecular targets, in particular proteins, present on or in a biological analysis support, said method remedying all the abovementioned drawbacks.

To this effect, the measurement method according to the invention comprises the following steps:

a) the measuring points of the support are scanned by moving, focusing and superimposing at least two laser beams on each measuring point of this support by simultaneous intersection of these beams, so as to extract therefrom a contained hot plasma comprising at least one chemical element to be quantified, present in said targets, and at least one other chemical element exogenous to these targets and present in a known amount on or in this supporting, b) light emission lines from each plasma which correspond to the or to each element to be quantified and to the or to each exogenous element are detected and analyzed, for each of these measuring points, by measuring the respective intensities of these lines, and then c) the concentration in each measuring point of the or of each element to be quantified or of a group incorporating it within these targets is determined via a prior calibration of the lines of the or of each element to be quantified establishing a correlation between the intensities of the lines specific to this element to be quantified and the concentrations of the latter in mixtures of, in known proportions, of the or of each element to be quantified and of the or of each exogenous element.

The method according to the invention thus makes it possible to rapidly and efficiently "scan" (i.e. analyze in a sweep) all the measuring points of the biochip, at the same time being independent of a variation in the adjustment of the power of the lasers and in the sensitivity of the detection from one acquisition to the other, by virtue of the presence of an internal reference corresponding to the exogenous element, and to deduce, from the abovementioned step c), the number of atoms of the element being investigated in each measuring point, so as to deduce therefrom the number of targets at the coordinate observed, all in less than 1/1000 second per reading point on average (reading time=number of readings/acquisition time).

It will be noted that this focusing of several laser beams at a same point of the support which is carried out in step a) makes it possible to add their respective energies in order to generate a spectrally analyzable plasma.

It will also be noted that the correlation, used in step c), between line intensities y and concentration x for the exogenous element or for the element to be quantified is advantageously of linear type (i.e. a relationship of proportionality, to within one affinity constant, according to the equation y=ax+b).

According to another characteristic of the invention, said biomolecular targets are immobilized, prior to step a), at the surface or in the body of the biological analysis substrate, which is preferably substantially planar and is chosen from the group constituted of biochips, transfer membranes, silicon substrates, polyimide substrates (e.g. Kapton® substrates) and glass substrates, and electrophoresis and chromatography gels.

Advantageously, this support is formed from a biochip comprising, at its surface, an array of probes that are native, hybridized or complexed by said targets, this array comprising a multitude of said measuring points each comprising a plurality of probes, and the or each chemical element to be quantified being present in these targets and, optionally, also in these probes.

It will be noted that, when the element to be quantified is both in the probe and in the target, said exogenous element makes it possible to deduce the amount of signal which comes from the probe and the amount of signal which comes from the target. This exogenous element provides an internal calibration which makes it possible to readjust the signal to the calibration curves, irrespective of the signal attenuations due to the adjustment of the apparatus.

According to another characteristic of the invention, this measurement method also comprises a subsequent step of obtaining one or more representative images of the concentration of the or of each element to be quantified or of the or of each exogenous element, the intensity of each pixel or else of each of the three colors R, G, B of the latter within the image being representative of the intensity of the line of the corresponding element observed.

The resulting image thus makes it possible to map the abundance of the or of each element to be quantified or exogenous element on or in the analysis support. The mapping of the body of the analysis support is obtained by successive shots in the same position, the signals obtained being either accumulated, or analyzed separately so as to perform a mapping along the Z-axis of the support, either averaged or in slices. The number of successive shots depends in particular on the desired analysis depth and on the physicochemical properties of the material of the support.

In the abovementioned case of a probe-array biochip, the immobilization, prior to step a), of the target molecule is obtained either directly by interaction with the material constituting the support or retention in the molecular mesh of the support, or indirectly by interaction with a ligand (probe) attached on or in the support. By way of such probe/target interactions, mention may, for example, be made of:

hybridization between a target and a probe of nucleic acid type or similar (e.g. PNA, LNA), protein/protein interactions between a target and a probe of protein type, such as ligand/receptor, antibody/bound antigen, nucleic acid or similar/protein mixed interactions, interactions of the type nucleic acid/metal, ion or any other free molecule, or interactions of the type protein/ion or any other free molecule.

Preferably, each laser beam used in step a) is emitted in the infrared-visible-ultraviolet range according to a pulse lasting between 1 fs and 100 ns, with a frequency of between 600 Hz and 1 GHz and an energy of between 0.05 mW and 1 kW.

Even more preferably, each laser beam is emitted in the ultraviolet range at a wavelength of 266 nm or 193 nm, using, for example, Nd:YAG laser (neodymium-doped yttrium aluminum garnet laser) harmonics, according to a pulse of duration less than 10 ns, preferably equal to 5 ns.

As a variant, the laser beams used in step a) can be emitted at different wavelengths, for example in the ultraviolet range at a wavelength of 266 nm and in the visible range at 532 nm, always according to a pulse of duration less than 10 ns and preferably equal to 5 ns.

According to another characteristic of the invention, said beams can advantageously be formed, in step a), in a scanning head, such that:

these beams are reflected tangentially on a deflecting pyramid with at least one reflection stage so as to give, on leaving this pyramid, collinear beams, these collinear beams pass through an afocal optical system, such as a beam-reducing telescope, which reduces the respective diameters of these beams and the distances separating them from one another, and then that these reduced collinear beams are subsequently focused and intersected on each measuring point by planar, parabolic or ellipsoidal mirrors arranged at the outlet of said scanning head.

Advantageously, said reduced collinear beams can be focused and intersected on each measuring point of said support by two optical rotating disks with mirrors deflecting them, respectively, in horizontal and vertical directions, and preferably by a deviation periscope coupled to these disks.

It will be noted that the superimposition by intersection of the laser beams generates, in step a), a power density in each measuring point advantageously greater than $0.5 \text{ GW} \cdot \text{cm}^{-2}$, for obtaining, by vaporization, a hot plasma which has a lifetime of approximately 2 μs.

Advantageously, a single intersection of two laser beams can be used to ablate each measuring point, having a surface area of between 1 μm$^2$ and 10 000 μm$^2$. The scanning of all the measuring points, according to a fixed step, must be carried out using mirrors, preferably ellipsoidal mirrors, which move, focus and intersect with the beams on the surface to be analyzed.

Preferably, at least one activating agent formed from a plasmagenic gas, such as argon, helium or nitrogen or a mixture of these gases, is added to each contained plasma.

According to a first preferred embodiment of the invention, the extracted plasmas are respectively optically contained in chambers for integration of the light emitted by the corresponding plasma which each have a reflecting sidewall and which are each provided with at least one optical fiber for acquisition of the light accumulated in this chamber, such that each plasma does not interfere with the other measuring points to be analyzed.

In accordance with this first embodiment, the biological analysis support is subjected, during step a), to a relative movement with respect to the optical containment chambers at the same time as said laser beams are made to intersect, and these chambers are then preferably guided above said support which remains fixed. As a variant, it is possible to use a mutual overlapping of the respective optical apertures of the acquisition optical fibers by arranging them in staggered rows above said support, so as to cover the entire surface to be analyzed of said support, without relative movement of these chambers with respect to said support.

According to a second embodiment of the invention, said chambers for optical containment of the extracted plasmas are themselves housed in a closed enclosure which contains the support, which is filled with plasmagenic gas and at least the upper face of which is transparent to the or each excitation wavelength of the laser beams and to the wavelengths for acquisition of the light generated by this plasma. In accordance with this second embodiment, it will be noted that it is possible to move said laser beams simultaneously, the movement being relative to said support.

According to another characteristic of the invention, the laser induced breakdown spectroscopy (LIBS) technique is advantageously used for carrying out steps a) to c), and the laser induced fluorescence (LIF) technique is preferably used in parallel for these same steps.

According to another characteristic of the invention, the plasmas can be generated by means of parallel-ray X-ray radiation, the source of which is preferably a femtosecond or even nanosecond X-ray laser with a scan rate of between 5 Hz and several kHz. The convergence of the X-ray radiation is obtained by means of mirrors (parabolic, ellipsoidal, concave) capable of reflecting X-rays, such as mirrors constituted of a silicon plate coated with alternating layers of chromium and scandium. The incidence of the radiation is preferably glancing incidence at the surface of the mirror (i.e. radiation almost parallel to its surface), in order to enable considerable reflection.

In addition to the analysis of the plasma, the device equipped with such a source of X-rays allows an analysis of the X-ray fluorescence of the samples segregated at the surface or in the body of the biological analysis support. This is because, by virtue of these X-rays, the material—and in particular the phosphorus—contained in the samples re-emits energy in the form, inter alia, of X-rays and of other types of electromagnetic radiation; this is X-ray fluorescence or secondary emission of X-rays.

The analysis and the mapping of this X-ray fluorescence or of these other forms of radiation make it possible to rapidly and semiquantitatively map the sample at the surface of the support. This rapid analysis can make it possible, for example, to define the zones to be analyzed more finely by the LIBS technique. The acquisition of the X-ray fluorescence can be carried out using, in the device, optical fibers made of a doped polymer sensitive to X-rays. The doping agents used can be compounds which are luminescent under X-rays, and their introduction into the optical fiber converts the X-ray radiation into radiation that can be conducted by the fiber.

This same principle can be used for the selective acquisition of the emission lines of the elements targeted in the plasma, by introducing, into the acquisition optical fibers, a chemiluminescent, fluorescent, etc., doping element which is excitable only at the wavelength of the line targeted, and which re-emits at a wavelength which is, on the one hand, absent from the spectrum of the plasma and, on the other hand, well conducted by the fiber under consideration.

Advantageously, said biomolecular targets are chosen from the group constituted of unlabeled nucleic acids, proteins, peptides, polypeptides, polynucleotides such as DNA, and sugars. It will be noted that any other biological compound which can be characterized by such an element intrinsic to its structure or which binds strongly to the latter can, in general, be used as a target.

In the preferred case of a support of probe-array biochip type, these probes are chosen from the group constituted of nucleic acids, peptide nucleic acids (PNAs), locked nucleic acids (LNAs), ribonucleic ethers (ERNs), antibodies, half-antibodies, half-antibodies coupled with nucleic acids and protein receptors. It will be noted that any other biological compound which can bind specifically to a target and which can be immobilized on an analysis support can, in general, be used as a probe.

Advantageously, said or each exogenous element (i.e. which does not exist in the structure of the targets) is deposited in a known amount on the analysis support, either homogeneously or specifically with the probes. When they are deposited with the probes, these exogenous elements are either included in compounds which will be grafted onto the support together with the probes in known proportions, or directly implanted in the structure of the probe by atomic substitution or strong interaction. In an even more advantageous embodiment, the exogenous elements can be included in a molecular matrix which facilitates the formation of the plasma (i.e. substance with a high optical absorbance for the excitation wavelength and with a low ablation energy), this matrix being deposited homogeneously at the surface of the biological analysis support.

It may be advantageous to use PNA probes, in particular when the concentrations of the targets are very low. This is because the very high affinity of PNAs for nucleic acids makes it possible to trap all the oligonucleotide-type targets present in the medium to be analyzed.

Furthermore, since PNAs are capable of spontaneously binding to a gold surface by virtue of their COOH or NH end, these PNA molecules are particularly advantageous for deposits of probes on a plastic support of a biochip (e.g. made of Kapton® polyimide), coated with a layer of gold a few microns thick.

The fact that PNAs contain no phosphorus, and more generally no atom having a specific emission ray at 253 nm, at 194 nm or at 203 nm makes it possible to increase the detection sensitivity by completely eliminating the signal of the probe.

According to another characteristic of the invention, said or each chemical element to be quantified can be chosen from the group constituted of phosphorus, sulfur, iodine, nitrogen, oxygen and carbon.

Advantageously, use is made of nucleic acids or phosphorylated proteins as targets, and use is made of the phosphorus present in these targets as element to be quantified for the detection in the plasma, in step b), of phosphorus atomic and ionic emission rays. In this case, in step b), the phosphorus emission rays are detected at a wavelength having a value which is chosen from the group constituted of 138±3 nm, 148±3 nm, 154±3 nm, 167±3 nm, 177±3 nm, 190±3 nm, 193±3 nm, 203±3 nm, 213±3 nm and 253±3 nm, and which is preferably 203±3 nm.

Also advantageously, use is made of nucleic acids or proteins as targets and probes, and use is made of sulfur and iodine, respectively, in said targets and said probes as element to be quantified for the detection in the plasma, in step b), of atomic and ionic emission rays of sulfur and of iodine. In these two cases, the sulfur emission rays are detected, in step b), at a wavelength having a value which is chosen from the group constituted of 167±3 nm, 181±3 nm, 190±3 nm, 199±3 nm, 415±3 nm, 458±3 nm, 922±3 nm, 942±3 nm and 968±3 nm, and which is preferably 415±3 nm, and the iodine emission rays are detected at a wavelength having a value which is chosen from the group constituted of 150±3 nm, 161±3 nm, 170±3 nm, 178±3 nm, 183±3 nm, 511±3 nm, 661±3 nm, 740±3 nm, 746±3 nm, 804±3 nm, 839±3 nm, 902±3 nm, 905±3 nm, 911±3 nm and 973±3 nm, and which is preferably 511±3 nm.

Also, in the latter two cases, use is advantageously made of chlorine or bromine as element exogenous to said targets or to said probes, for the detection in the plasma, in step b), of atomic and ionic emission rays of sulfur and of iodine, respectively, in order to lift the indeterminate nature of the signals generated both by these probes and by these targets. The following are then detected in step b):

chlorine emission rays at a wavelength having a value chosen from the group constituted of 35±3 nm, 386±3 nm, 413±3 nm, 479±3 nm, 490±3 nm, 499±3 nm, 507±3 nm, 521±3 nm, 539±3 nm, 542±3 nm, 774±3 nm, 725±3 nm, 741±3 nm, 754±3 nm, 822±3 nm, 833±3 nm, 837±3 nm, 842±3 nm, 858±3 nm, 868±3 nm, 894±3 nm, 912±3 nm, 919±3 nm, 928±3 nm, 945±3 nm and 959±3 nm; or else bromine emission lines at a wavelength having a value chosen from the group constituted of 154±3 nm, 158±3 nm, 163±3 nm, 614±3 nm, 635±3 nm, 655±3 nm, 663±3 nm, 751±3 nm, 780±3 nm, 793±3 nm, 798±3 nm, 813±3 nm, 827±3 nm, 844±3 nm, 889±3 nm, 916±3 nm and 926±3 nm.

DNA is used for said targets and a cation bound to these targets and chosen from the group constituted of sodium, magnesium and potassium is used as element to be quantified, for the detection in the plasma, in step b) of phosphorus atomic and ionic emission rays. In this case, the following are detected in step b):

sodium emission rays at a wavelength having a value chosen from the group constituted of 268±3 nm, 285±3 nm, 291±3 nm, 292±3 nm, 298±3 nm, 314±3 nm, 321±3 nm, 325±3 nm, 330±3 nm, 353±3 nm, 363±3 nm, 449±3 nm, 466±3 nm, 497±3 nm, 569±3 nm, 589±3 nm, 616±3 nm and 819±3 nm; or magnesium emission rays at a wavelength having a value chosen from the group constituted of 285±3 nm, 880±3 nm, 309±3 nm, 333±3 nm, 383±3 nm, 457±3 nm, 473±3 nm, 518±3 nm, 552±3 nm, 571±3 nm, 925±3 nm, 964±3 nm and 941±3 nm; or else potassium emission rays at a wavelength having a value chosen from the group constituted of 404±3 nm, 535±3 nm, 580±3 nm, 693±3 nm, 766±3 nm, 769±3 nm, 825±3 nm, 850±3 nm, 890±3 nm and 959±3 nm.

According to one variant of the invention, use is advantageously made of the nitrogen and/or the carbon and/or the oxygen present in said targets and said probes as element(s) to be quantified for the detection in the plasma, in step b), of the atomic emission rays of nitrogen and/or of carbon and/or of oxygen in order to evaluate the amount of targets and of probes on said support, which contains neither carbon nor nitrogen nor oxygen. In this case, the following are detected in step b):

nitrogen emission rays at a wavelength having a value which is chosen from the group constituted of 174±3 nm, 575±3 nm, 744±3 nm, 821±3 nm, 859±3 nm, 865±3 nm, 871±3 nm, 938±3 nm and 870±3 nm, and which is preferably 575±3 nm;

carbon emission rays at a wavelength having a value which is chosen from the group constituted of 156±3 nm, 165±3 nm, 175±3 nm, 193±3 nm, 247±3 nm, 538±3 nm, 600±3 nm, 711±3 nm, 833±3 nm, 908±3 nm, 911±3 nm, 965±3 nm and 940±3 nm, and which is preferably 600±3 nm; and/or oxygen emission rays at a wavelength having a value which is chosen from the group constituted of 615±3 nm, 645±3 nm, 700±3 nm, 725±3 nm, 777±3 nm, 822±3 nm, 844±3 nm and 926±3 nm, and which is preferably 615±3 nm.

It will be noted that the nitrogen and/or the carbon and/or the oxygen present in all the biological targets and probes as element(s) to be quantified for the detection in the plasma, in step b), of the atomic emission rays of these elements, thus make(s) it possible to evaluate the amount of overall material (i.e. probes+targets) present on the support, on the abovementioned condition that the support does not contain any carbon, nitrogen or oxygen.

In order to improve the detection limits, it is advantageously possible:
(i) to implement the LIBS technique by performing a double laser pulse of the double pulse LIBS type, and/or
(ii) to use this LIBS technique in parallel with the LIF technique (i.e. an LIBS-LIF combination), and/or
(iii) to subject the contained plasma and/or the surface of the material to microwave radiation capable of heating the polar molecules represented by the biomolecules.

Via these three preferred methods (i), (ii) and (iii), a more ready induction of each plasma and an increase in the intensity and the lifetime of the atomic emission rays of the targeted elements are in particular achieved, this making it possible to obtain a better signal-to-noise ratio and thus to decrease by a factor at least equal to ten the detection threshold for said element to be quantified and therefore for the targets from which it is derived.

With regard specifically to this double laser pulse method (i), it can be carried out with two other intersected beams for the second pulse (power, frequency, wavelength), of the same nature as those of the first pulses. This is because, given the lifetime of approximately 2 µs of the plasma, the latter is optically analyzable from approximately 100 ns after its formation (end of the black-body radiation and the emergence of the atomic and ionic lines sought).

This second laser pulse, shortly before its extinction, makes it possible to prolong the lifetime of the plasma and to amplify the emission emitted. A wavelength characteristic of the atom for which the atom(s) targeted has (have) a strong absorption or emission is advantageously chosen. It is thus possible to increase the light emission from the ions and/or from the atoms targeted (in this case phosphorus), by exciting their own specific fluorescence with this second laser pulse.

According to another characteristic of the method according to the invention, the ablation of material at the surface of the biological analysis support and the formation of the plasma can be uncoupled. In this case, a first UV laser pulse ablates a part of the surface of the biochip and ejects it above the latter, and then a second pulse advantageously using a laser of femtosecond type at a frequency of from 600 Hz to 1 GHz creates the plasma and generates the characteristic emission of its constituents. Optionally, a third pulse can then be used in order to excite the fluorescence of the compounds targeted.

The method according to the invention thus makes it possible to efficiently and rapidly detect biomolecular targets without labeling the latter, in particular on the basis of the fluorescence of the atoms constituting the nucleic acid molecules after the emission of a plasma. In order to have a truly quantitative measurement of these nucleic acid molecules, the abovementioned calibration of the targets is necessarily carried out via standardization of their respective sizes.

A device according to the invention for implementing the abovementioned method for quantitative measurement comprises:
- a biological analysis support, which is preferably substantially planar, such as a biochip, for example a probe-array biochip, a transfer membrane or an electrophoresis or chromatography gel,
- a plasma generating unit which comprises means for focusing and superimposing on each measuring point at least two laser beams by simultaneous intersection of these beams on this support so as to extract them from a hot plasma containing at least one chemical element to be quantified, such as phosphorus, which is present in the targets, these means for focusing and superimposing the beams comprising a scanning head capable of forming them in a collinear manner and a system of mirrors arranged at the outlet of this head, which cooperates with optical rotating disks with mirrors so as to deflect the beams toward the support so as to scan the measuring points of the latter,
- means for optical containment of each plasma extracted by this plasma generating unit, arranged above this support, and
- a spectrography unit which is connected to these containment means by acquisition optical fibers which emerge into said containment means, and which is suitable for detecting and analyzing emission light lines from the plasma extracted for each measuring point, such that the concentration, in each measuring point, of said element(s) to be quantified is determined on the basis of one of the intensities of these lines and on the basis of calibration curves.

According to another characteristic of the invention, said means for focusing and superimposing the beams can essentially comprise:
- said scanning head which comprises:
  - an upside-down deflecting pyramid comprising at least one stage designed to tangentially reflect incident beams emitted by several laser sources so as to make them collinear on leaving this pyramid, and
  - an afocal optical system arranged below the tip of this pyramid, preferably a beam-reducing telescope, designed so as to receive these collinear beams while reducing their diameters and the distances separating them from one another, and
- said system of planar, parabolic or ellipsoidal mirrors which cooperates with said optical rotating disks with mirrors deflecting them in horizontal and vertical directions, and preferably which also cooperates with a deviation periscope coupled to these disks so that the collinear beams reduced by this afocal system are focused and intersected on each measuring point.

According to the abovementioned first embodiment of the invention, said containment means are capable of optically containing each extracted plasma and comprise a plurality of open chambers which are each delimited by a side wall arranged perpendicularly to said support, the internal face of this wall being capable of reflecting the light accumulated in this chamber and in particular the wavelengths of the lines from said chemical elements to be quantified, and at least one of said acquisition optical fibers passing through this wall.

According to a first example of this first embodiment of the invention, said means for optical containment of each plasma can comprise a plurality of adjacent rings for integration of the light emitted by this plasma, said sidewall having a substantially circular cross section, the free end of several of said acquisition fibers emerging inside the chamber formed by each ring via orifices made in said wall.

According to a second example of this first embodiment of the invention, said means for optical containment of each plasma can comprise a plurality of chambers for integration of the light emitted by this plasma, said sidewall of each chamber having a cross section substantially in the form of an equilateral triangle and these chambers being contiguous in pairs via one of their sides, with each chamber being provided with said acquisition fibers at each of their three vertices.

In accordance with these first and second examples, means for relative movement of the chambers with respect to the support, such as rails for sliding said chambers equipped with electromagnets, are advantageously provided so as to cover the entire surface, of the support, to be analyzed.

According to a third example of this first embodiment of the invention, said means for optical containment of each plasma can comprise a plurality of chambers for integration of the light emitted by this plasma, which are equipped with at least two series of acquisition fibers arranged in staggered rows, the respective optical apertures of which are capable of covering, by mutual overlapping, the entire surface, of said support, to be analyzed.

In this third example, the device according to the invention then does not use relative movement of the optical containment chambers with respect to the analysis support.

According to the abovementioned second embodiment of the invention, said chambers for optical containment of the extracted plasmas are themselves housed in a closed enclosure which contains the support and which is filled with a plasmagenic gas such as argon, helium, nitrogen or a mixture of these gases, at least the upper face of this enclosure being transparent to the or each excitation wavelength of the laser beams and to the wavelengths of acquisition of the light generated by this plasma, this enclosure being equipped with a valve for filling with a plasmagenic gas and a valve for flushing of air.

As indicated above, the biological analysis support used in relation to the device according to the invention is preferably formed from a biochip comprising, at its surface, an array of probes which are native, or hybridized or complexed by said targets, this array comprising a multitude of said measuring points, each comprising a plurality of said probes, and said or each chemical element to be quantified being present in these targets and, optionally, also in these probes.

According to another characteristic of the invention, said spectrography unit comprises at least one spectrograph of photo multiplier type, and an optical filter which is transparent only to the desired wavelength can be placed between each acquisition optical fiber and said spectrograph.

According to another preferred characteristic of the invention, the spectrography unit comprises at least one detector of photo multiplier type. It will, however, be noted that a camera of CCD (charge coupled device) or intensified CCD type or else a "wafer" of microchannels could also be used for the detection of the plasma emission lines.

Also preferably, an optical filter which is transparent only to the desired wavelength can be placed between each acquisition optical fiber and the spectrograph.

In one preferred embodiment, each of the acquisition optical fibers coming from the optical containment means (i.e. each "mother" fiber) divides up into as many fibers as there are wavelengths for elements to be observed. Each "mother" fiber is arranged in a beam opposite a detector which can be a photosensitive cell such as a photo multiplier (abbreviated to PM), a Channel Tron, a "wafer" of microchannels, etc. An optical filter which selects only the desired wavelength can be inserted between each acquisition optical fiber and the detector, for injecting the light into the latter. In addition, an appropriate lens can be attached at the output of each optical fiber.

In general, it will be noted that these filters can advantageously be replaced with diffraction gratings.

BRIEF DESCRIPTION OF THE DRAWINGS

The abovementioned characteristics of the present invention, and also others, will be understood more clearly on reading the following description of several exemplary embodiments of the invention, given by way of nonlimiting illustration, said description being given in relation to the attached drawings, among which:

FIG. 4 is a partial schematic view, from above, of the analysis support of FIG. 1 which is surmounted by means for optical containment of the plasmas respectively generated in various measuring points, according to an example of a first embodiment of the invention, FIG. 5 is a schematic view in vertical section according to the plane of section V-V of FIG. 4, of one of these containment means, FIG. 6 is a schematic view in vertical section according to a variant of FIG. 5, of one of these optical containment means arranged above the analysis support, FIG. 7 is a schematic view in vertical section according to another variant of FIG. 5, of such an optical containment means, FIG. 8 is a schematic view in vertical section according to another variant of FIG. 5, of such an optical containment means, FIG. 9 is a partial schematic view, from above, of the analysis support of FIG. 1 surmounted by means for optical containment of the plasmas according to another example of this first embodiment of the invention, FIG. 10 is a partial schematic view, from above, of the analysis support of FIG. 1 surmounted by means for optical containment of the plasmas according to another example of this first embodiment of the invention.

DETAILED DESCRIPTION OF THE INVENTION

Figures 1, 2, 3:
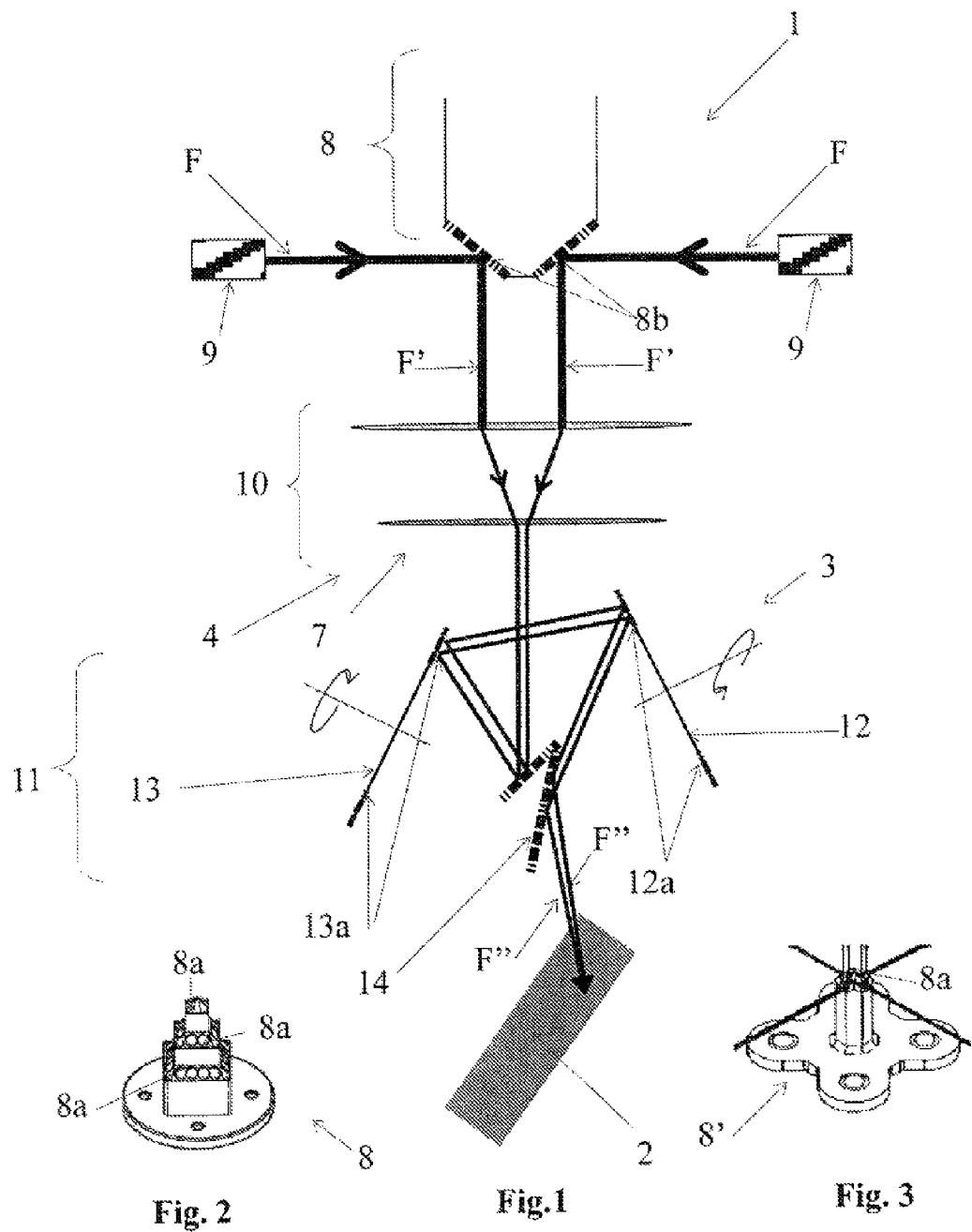
FIG. 1 is a schematic side view of a plasma generating unit which is included in a device for quantitative measurement according to the invention and which is illustrated in relation to a biological analysis support incorporating the biomolecular targets to be quantified.
FIG. 2 is a partially sectional and perspective schematic view of an optical deflecting pyramid included in a laser scanning head of the plasma generating unit of FIG. 1.
FIG. 3 is a perspective schematic view of a simplified variant of the deflecting pyramid according to FIG. 2.

The device 1 for quantitative measurement, according to the invention, of biomolecular targets comprises:
  a biological analysis support 2, which is preferably substantially planar, such as a biochip, for example a probe-array biochip, a transfer membrane or an electrophoresis or chromatography gel,
  a plasma generating unit 3 (see FIG. 1) which comprises means 4 for focusing and superimposing on each measuring point at least two laser beams by simultaneous intersection of these beams on this support 2 so as to extract therefrom a hot plasma P (visible in FIGS. 5 and 13) containing at least one chemical element to be quantified present in these targets,
  means for containment 5 of each plasma P extracted by this unit 3, arranged above the support 2 (see FIG. 4 and seq.), and
  a spectrography unit (not illustrated) which is connected to these containment means 5, 5', 5" by acquisition optical fibers 6, 6', 6" (visible in FIG. 4 and seq.) which emerge into these containment means 5, 5', 5", and which is suitable for detecting and analyzing emission light lines from the plasma P extracted for each measuring point, in such a way that the concentration in each measuring point of the element to be quantified is determined on the basis of one of the intensities of these lines and on the basis of calibration curves.

The means 4 for focusing the laser beams F on each measuring point essentially comprise, with reference to FIG. 1:
  a scanning head 7 which is capable of forming these beams F in a collinear manner and which comprises:
    an upside-down deflecting pyramid 8 comprising at least one stage 8a designed so as to tangentially reflect incident beams F emitted by several laser sources 9 so as to make them collinear on leaving this pyramid 8, via high-quality aluminum mirrors 8b, and
    an afocal optical system 10 arranged below the tip of this pyramid 8, preferably a beam-reducing telescope, which is designed so as to receive these collinear beams F' by reducing their respective diameters and the distances separating them from one another, and
  a system of planar, parabolic or ellipsoidal mirrors 11 which is arranged at the outlet of the scanning head 7 and which cooperates with optical rotating disks 12 and 13 with mirrors 12a and 13a deflecting them in horizontal and vertical directions and, preferably, which also cooperates with a deviation periscope 14 coupled to these disks 12 and 13 so that the collinear beams F' reduced by this afocal system 10 are focused and intersected on each measuring point.

This scanning head 7 is used as follows.

The various laser beams F (of which there are two in the example of FIG. 1) are reflected tangentially on the high-quality mirrors 8b of the deflecting pyramid 8 which provide their collinearity, for any angle of the direction of incidence of these beams F (preferably, this angle is equal to 90°).

As illustrated in FIGS. 2 and 3, the deflecting pyramid 8, 8' can have a single stage 8a (FIG. 3) using, for example, four distinct laser sources 9, or else several stages 8a which can typically range up to five (FIG. 2) using, in this case, for example, a maximum of one hundred laser sources 9 in parallel.

It should be noted that the increase in the number of sources 9 makes it possible in particular to increase the scanning resolution, with a greater spatial coverage by the beams on the scanning zone.

On leaving the pyramid 8, the collinear beams F' pass through the beam-reducing telescope 10 constituted of a system of multiple superimposed lenses which reduce the diameter and the distance separating these collinear beams F' from one another. For example, beams F' having a diameter of 2 mm and separated by 2.5 mm on leaving the pyramid 8 are reduced, on leaving the telescope 10, to a diameter of 500 μm and a separation of 500 μm.

Once reduced, these collinear beams F' are then scanned over the analysis support 2 by means of the two horizontal 12 and vertical 13 optical rotating disks (ORDs) with mirrors 12a and 13a providing, respectively, horizontal and vertical deflections of the beams, and also the deviation periscope 14. These optical disks 12 and 13 can be, as required, of single-track or multitrack type (i.e. with one or more concentric rows of mirrors), according to the number of sources 9, to the hindrance, to the resolution, etc. The device for measurement 1 according to the invention also comprises an electronic control system (not illustrated) for managing and precisely controlling the rotational speeds of these optical disks 12 and 13.

It will be noted that the reduction in the optical unit of the laser beams F' by the telescope 10 makes it possible to make all these beams F' reflect on the single mirror 12a of the horizontal rotating disk 12 and the single mirror 13a of the vertical rotating disk 13, in order to make them converge toward an identical point at the surface of the support 2. Each mirror 12a, 13a is in fact positioned in a unique manner on the rotating disks 12 and 13 in terms of angle of incline, so as to make the various beams F" converge toward a clearly localized zone of the support 2.

For reasons of hindrance, the distance between the two rotating disks 12 and 13 is preferably reduced by the addition of the deviation periscope 14 which adds two additional reflections to the course of the beams.

The focusing of the various beams F" on the support 2 can be provided by the afocal system 10, adjusting in particular the separation of the optics, by parabolic mirrors which are positioned on the vertical optical rotating disk 13 located at the outlet of the scanning head 7, by an ancillary system composed of focusing lenses and/or mirrors at the outlet of the scanning head 7, adjusting the incline of the mirrors of the pyramid so as to make the beams F' intended to intersect slightly noncollinear.

In certain embodiments, with a configuration using groups of at least two beams, only the beams of each group intended to be intersected on the support 2 will be collinear, such that only the collinear beams of each group converge at a same point of the support 2.

At the outlet of this scanning head 7, each laser beam F" is focused on the surface to be analyzed of the support 2 by the mirrors of the head 7 and the beams are intersected at at least one measuring point of this surface. The intersection of each beam presents a power or irradiance density at the surface of each measuring point which is greater than 0.5 GW·cm$^{-2}$, which is sufficient to obtain, by vaporization, a hot plasma P having a lifetime of approximately 2 μs, in general with a threshold power per unit of surface area greater than the threshold for ablation of the material of the support.

At these very high energy densities, a part of the material of each measuring point is in fact ejected from the surface to be analyzed by vaporization, and this hot plasma P, which is very luminous and has a very short lifetime, is thus generated. This ablated material in the form of plasma P is dissociated into its various atomic and ionic constituents and, at the end of each laser pulse, this plasma P cools rapidly. During this period, the excited atoms and ions emit light radiations which are characteristic thereto, owing to their return to lower energy levels.

FIGS. 4 to 12 illustrate examples of structures that can be used for the optical containment means 5, 5', 5" for each plasma P generated, so that it does not interfere with the other measuring points to be analyzed, before simultaneous detection of the emission lines from the plasma P corresponding to each intersection of beams. As indicated above, the optical analysis of the plasma P generated point-by-point at the surface of the biological analysis support 2 makes it possible to reconstitute an image in each measuring point of the amount of atoms of the element analyzed, making it possible to deduce therefrom the number of targets according to the abundance of the element in the molecular formula of the target.

As illustrated in FIG. 4, the emission lines from the plasma P generated in each measuring point can, for example, be captured by several acquisition optical fibers 6 (at least three optical fibers 6), the respective free ends of which are arranged evenly on a circular ring 5 of 1 to 20 cm in diameter and with a low height, which is designed so as to optically isolate this plasma P. The internal face of the sidewall 5a, 5b, 5c of this ring 5 constitutes a mirror which may be concave (see FIGS. 5 and 6), multifaceted (see FIG. 7), planar (FIG. 8), ellipsoidal or even parabolic, provided that it is capable of reflecting the wavelengths of the lines of the elements of interest, thus forming an emitted light integration ring. The curvatures or inclines of the mirrors are preferably designed so as to make the light converge toward the opposite interior face of the ring 5.

The ring 5 is pierced at regular intervals with orifices 5d on its sidewall 5a, 5b, 5c (e.g. cylindrical in the example of FIG. 5) so as to receive the acquisition optical fibers 6. Owing to its numerical aperture, each acquisition fiber 6 can be capped with a set of appropriate lenses, such as a fiber collimator, for correctly injecting the radiation emitted by the plasma P into the spectrography unit, the fields respectively viewed by the fibers 6 thus capped with corrective lenses, or optical apertures, mutually overlapping so as to form a surface comparable to a circle (or to a polygon lying within a circle), i.e. an optical circle 16. Each plasma P is generated in this optical circle 16, which is such that the cumulative optical path of the light from the plasma P to the fibers 6 is constant irrespective of the position of the plasma P in this circle 16.

In the variant of FIG. 9, the chambers 5' for optical containment of the plasma P each have the shape of an equilateral triangle and each have the same type of internal face of sidewall 5a' as the abovementioned rings 5. At the three vertices of each triangle 5', there are respectively three acquisition optical fibers 6' with, for each one, an optical aperture of greater than or equal to 60°, so as to capture the direct light from the corresponding plasma P and that which is reflected on the walls of the triangle 5'. A series of such equilateral triangles 5' can advantageously be arranged in such a way as to make a parallelogram encompassing the entire surface of the support 2.

Thus, the laser beams, intersected, converged and displaced by the abovementioned mirrors, scan, with the desired step, the whole of each optical circle 16 according to FIG. 4 or of each optical triangle 5' according to FIG. 9, generating, in each point, a plasma P of which the light is captured by all the associated acquisition fibers 6, 6'. It will be noted that the cumulative light which is captured by the fibers 6 of each optical circle 16 or those 6' of each optical triangle 5' has an intensity independent of the position of the plasma P in this optical circle 16 or optical triangle 5', respectively.

This method allows the scanning of the entire surface to be analyzed by the intersected laser beams with, for example, a step of 10 μm which corresponds to the zone ablated at each laser pulse, the optical containment chambers 5, 5' allowing the simultaneous acquisition of several plasmas P.

In order to allow the analysis of the surfaces at the base of the walls 5a, 5b, 5c or 5a' of these optical containment chambers 5, 5', it is necessary to carry out a relative movement of the biological analysis support 2 with respect to these chambers 5, 5', which is preferably carried out by moving the latter relative to the analysis support 2 which remains fixed.

Figure 11:
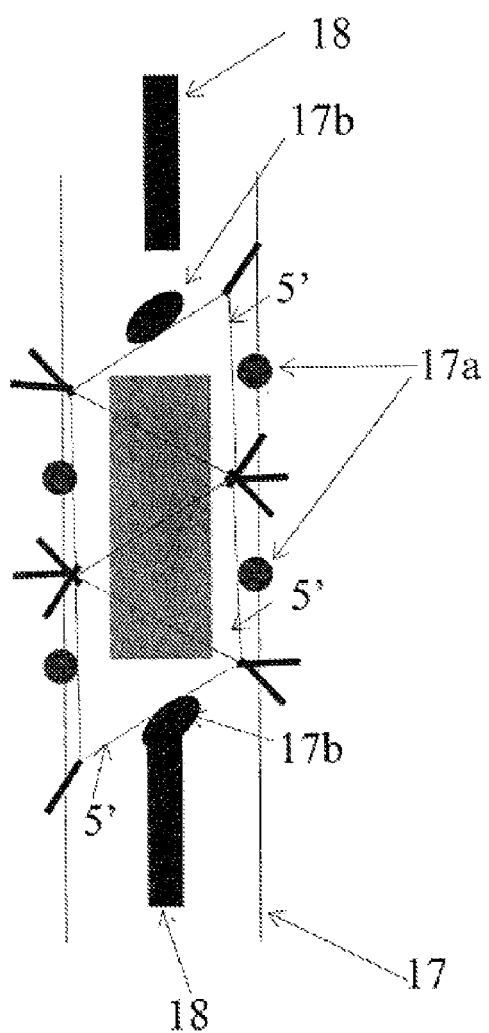
FIG. 11 is a partial schematic view, from above, of the analysis support of FIG. 1 surmounted by optical containment means according to the example of FIG. 9, also illustrating control members for moving these containment means with respect to this support in a given position.
Figure 12:
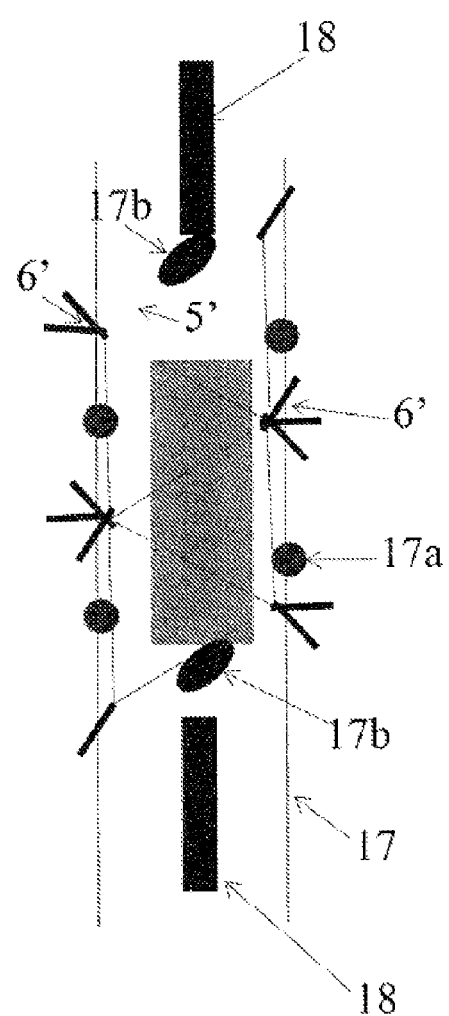
FIG. 12 is a view analagous to FIG. 11, showing these control members for moving the containment means in another operating position.

As illustrated in FIGS. 11 and 12, these optical containment chambers 5' (in this example triangular chambers) can slide along guides or rails 17 via supporting members 17a of the latter arranged on each side of the analysis support 2, under the control of two electromagnets 18 which are arranged outside and on either side of the support 2 and which alternately attract these chambers 5, 5', respectively in combination with two metal stops 17b for these electromagnets 18.

In the variant of FIG. 10, an analysis of the surface of the support 2 is carried out without relative movement of the optical containment chambers 5" with respect to the support 2, by arranging the acquisition optical fibers 6" in staggered rows laterally on either side of the support 2. By virtue of this arrangement, the whole of the respective optical apertures of the acquisition fibers 6" encompasses the entire surface of the support 2. A slight overlap 19 of the optical apertures of the optical fibers 6" laterally on either side of the support 2 thus allows the analysis of the surfaces located at the base of the limits of these optical apertures.

Figure 13:
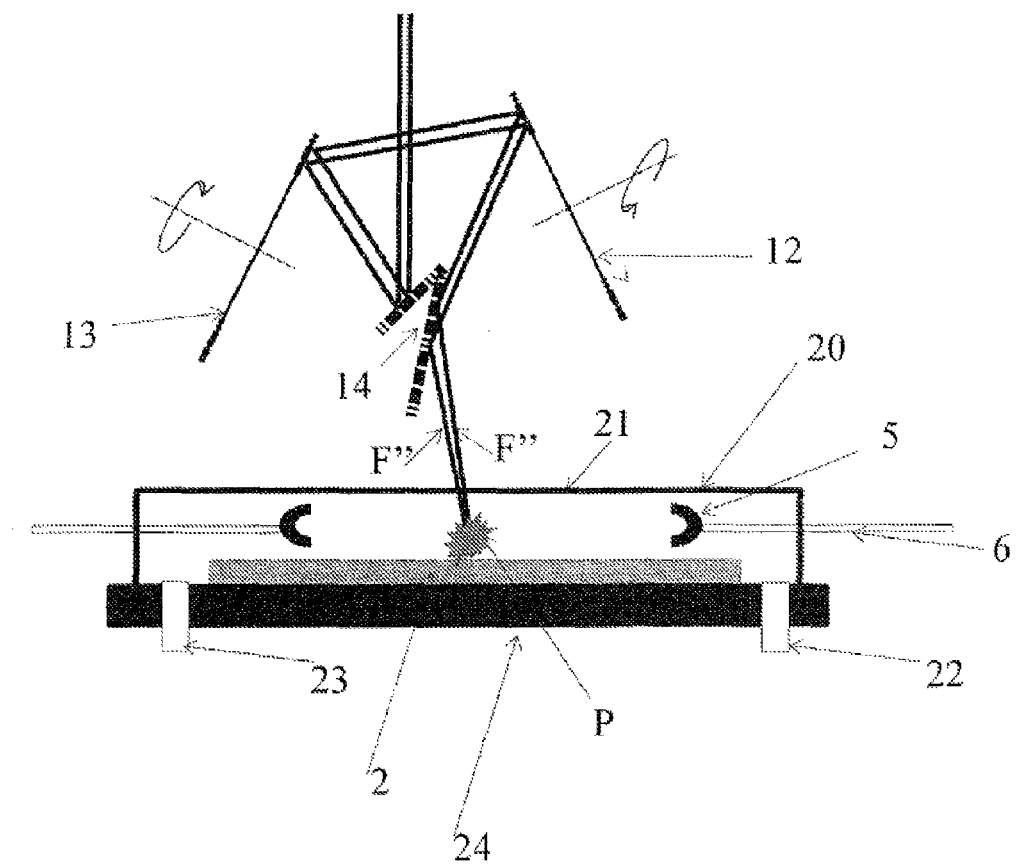
FIG. 13 is a schematic side view of the analysis support of FIG. 1 which is housed in means for containment of the plasmas according to a second embodiment of the invention, said enclosure being illustrated with a part of the adjacent plasma generating unit.

According to another embodiment of the invention illustrated in FIG. 13, the support 2 to be analyzed and also the abovementioned optical containment means 5, 5' (in this example constituted of the rings 5) are all arranged in a closed enclosure 20, at least the upper face 21 of which is provided transparent to the excitation wavelengths of the laser beams and to the acquisition wavelengths for the light generated by this plasma P. The air contained in this chamber 5 is removed by means of a valve for flushing of air 22, and then the chamber is filled with a plasmagenic gas (e.g. argon/nitrogen, helium) by means of a filling valve 23, these valves 22 and 23 being mounted in the lower face of support 24 of the enclosure 20.

In conclusion, it will be noted that the optical analysis of the plasma P generated point-by-point at the surface of the support 2 makes it possible to reconstitute an image of the amount of atoms of the element being sought, in each measuring point.

By using more than two lasers, it is also possible to simultaneously generate several plasmas P on the biological support 2 to be analyzed. Under these conditions, one optical containment unit is provided per plasma generated. The zones of the support 2 which are masked by this unit can be analyzed after a relative translation of these zones inside the optical containment unit, such as the abovementioned optical circle 5 or optical triangle 5'.

It will be noted that the geometries described for the LIBS mapping of the biological analysis supports are also applicable to LIBS mappings of relatively planar surfaces comprising nonbiological (inorganic or organic) supports to be analyzed.

The invention claimed is:

1. A method of high speed quantitative measurement of biomolecular targets present on or in a biological analysis support (2), comprising:
    (a) scanning measuring points of the support by moving, focusing and superimposing at least two laser beams (F") on each measuring point by simultaneous intersection of these beams to extract therefrom a contained hot plasma (P), the plasma comprising:
    at least one chemical element which is to be quantified and which is present in said targets, and
    at least one other chemical element which is exogenous to these targets and which is present in a known amount on or in this support,
    (b) detecting and analyzing light emission lines from each plasma which correspond to the or to each element to be quantified and to the or to each exogenous element for each of these measuring points, by measuring the respective intensities of these lines, and
    (c) determining the concentration in each measuring point of the or of each element to be quantified or of a group incorporating the element to be quantified within the targets via a prior calibration of the lines of the or of each element to be quantified establishing a correlation between the intensities of the lines specific to this element to be quantified and the concentrations of the element to be quantified in mixtures, in known proportions, of the or of each element to be quantified and of the or of each exogenous element.

2. The method as claimed in claim 1, further comprising a subsequent step of obtaining a representative image of the concentration of said or of each element to be quantified or of said at least on other chemical element exogenous to the targets, this image comprising pixels, the intensity of each of these pixels or else of each of the three colors of the pixels within this image being representative of the intensity of the line from the corresponding element observed.

3. The method as claimed in claim 1, wherein each of said laser beams (F) used in step (a) is emitted in the infrared-visible-ultraviolet range according to a pulse with a duration of between 1 fs and 100 ns, with a frequency of between 600 Hz and 1 GHz and an energy of between 0.05 mW and 1 kW.

4. The method as claimed in claim 3, wherein said laser beams (F) are emitted according to a pulse with a duration of less than 10 ns.

5. The method as claimed in claim 1, wherein said beams (F") are formed in step (a) in a scanning head (7), and:
    said beams are reflected tangentially on a deflecting pyramid (8) with at least one reflection stage (8a) to give, on leaving this pyramid, collinear beams (F'),
    said collinear beams pass through an afocal optical system (10), which reduces the respective diameters of these beams and the distances separating them from one another, and then that
    said collinear beams which have been reduced are subsequently focused and intersected on each measuring point by planar, parabolic or ellipsoidal mirrors (11) arranged at the outlet of said scanning head.

6. The method as claimed in claim 5, wherein said collinear beams (F') which have been reduced are focused and intersected on each measuring point of said support (2) by two optical rotating disks (12 and 13) with mirrors (12a and 13a) deflecting them respectively in horizontal and vertical directions.

7. The method as claimed in claim 5, wherein the superimposition by intersection of said laser beams (F") carried out in step (a) generates a power density in each measuring point which is greater than 0.5 GW·cm−2, for obtaining, by vaporization, each hot plasma (P) which has a lifetime of approximately 2 μs.

8. The method as claimed in claim 1, wherein at least one activating agent formed from a plasmagenic gas is added to each contained plasma (P).

9. The method as claimed in claim 1, wherein said contained hot plasmas (P) are respectively optically contained in chambers (5, 5', 5") for integration of the light emitted by the corresponding plasma, which each have a reflecting sidewall (5a, 5b, 5c, 5a') and which are each provided with at least one optical fiber (6, 6', 6") for acquisition of the light accumulated in this chamber, such that each plasma does not interfere with the other measuring points to be analyzed.

10. The method as claimed in claim 9, wherein said biological analysis support (2) is subjected, during step (a), to a relative movement with respect to the optical containment chambers (5, 5'), at the same time as said laser beams (F") are made to intersect.

11. The method as claimed in claim 9, wherein a mutual overlapping (19) of the respective optical apertures of said acquisition optical fibers (6") is used, by arranging said fibers in staggered rows above the support (2) to cover the entire surface of the support, to be analyzed without relative movement of these chambers (5") with respect to said support.

12. The method as claimed in claim 9, wherein said chambers (5') for optical containment of the contained hot plasmas (P) are themselves housed in a closed enclosure (20) which contains said support (2), which is filled with said plasmagenic gas and at least the upper face (21) of which is transparent to the or each excitation wavelength of said laser beams and to the acquisition wavelengths for the light generated by this plasma.

13. The method as claimed in claim 1, wherein a laser-induced breakdown spectroscopy (LIBS) technique is used for carrying out steps (a) to (c) with the use, in parallel, of a laser induced fluorescence (LIF) technique.

14. The method as claimed in claim 1, wherein said biomolecular targets are chosen from the group consisting of unlabeled nucleic acids, proteins, peptides, polypeptides, polynucleotides and sugars.

15. The method as claimed in claim 1, wherein said biomolecular targets are immobilized, prior to step a), at the surface or in the body of said support (2), which is substantially planar and is chosen from the group consisting of biochips, transfer membranes, silicon, polyimide and glass substrates, and electrophoresis and chromatography gels.

16. The method as claimed in claim 15, wherein said biological analysis support (2) is formed from a biochip comprising, at its surface, an array of probes that are native, hybridized or complexed by said targets, this array comprising a multitude of said measuring points each comprising a plurality of said probes, and said or each chemical element to be quantified being present in said targets and also in said probes.

17. The method as claimed in claim 16, wherein said probes are chosen from the group consisting of nucleic acids, peptide nucleic acids (PNAs), locked nucleic acids (LNAs), ribonucleic ethers (ERNs), antibodies, half-antibodies, half-antibodies coupled with nucleic acids and protein receptors.

18. The method as claimed in claim 16, wherein said biomolecular targets are immobilized, prior to step a), by means of probe/target interactions which are:
both based on proteins,
nucleic acid or the like/protein mixed interactions,
interactions of the type nucleic acid/metal, ion or any other free molecule, or
interactions of the type protein/ion or any other free molecule.

19. The method as claimed in claim 1, wherein said at least one other chemical element which is exogenous to the targets is deposited homogeneously in a known amount on said analysis support (2).

20. The method as claimed in claim 16, wherein said at least one other chemical element which is exogenous to the targets is deposited in a known amount on said analysis support (2) specifically with said probes, said at least one other chemical element being included in compounds grafted onto this support together with the probes in known proportions, or directly implanted in the structure of each probe by atomic substitution or strong interaction.

21. The method as claimed in claim 1, wherein said or each chemical element to be quantified is chosen from the group consisting of phosphorus, sulfur, iodine, nitrogen, oxygen and carbon.

22. The method as claimed in claim 21, wherein nucleic acids or phosphorylated proteins are used as targets, and the phosphorus present in these targets is used as the element to be quantified for the detection in the plasma, in step b), of phosphorus atomic and ionic emission lines.

23. The method as claimed in claim 22, wherein, in step (b), the phosphorus emission lines are detected at a wavelength with a value which is chosen from the group consisting of 138±3 nm, 148±3 nm, 154±3 nm, 167±3 nm, 177±3 nm, 190±3 nm, 193±3 nm, 203±3 nm, 213±3 nm and 253±3 nm.

24. The method as claimed in claim 16, wherein nucleic acids, labeled with sulfur or with iodine, or proteins are used as targets and probes, and sulfur and iodine, respectively, in said targets and said probes are used as the element to be quantified for the detection in the plasma (P), in step b), of atomic and ionic emission lines of sulfur and iodine.

25. The method as claimed in claim 24, wherein, in step (b), the sulfur emission lines are detected at a wavelength with a value which is chosen from the group consisting of 167±3 nm, 181±3 nm, 190±3 nm, 199±3 nm, 415±3 nm, 458±3 nm, 922±3 nm, 942±3 nm and 968±3 nm, and the iodine emission lines are detected at a wavelength with a value which is chosen from the group consisting of 150±3 nm, 161±3 nm, 170±3 nm, 178±3 nm, 183±3 nm, 511±3 nm, 661±3 nm, 740±3 nm, 746±3 nm, 804±3 nm, 839±3 nm, 902±3 nm, 905±3 nm, 911±3 nm and 973±3 nm.

26. The method as claimed in claim 24, wherein chlorine or bromine is used as said at least one chemical element exogenous to said targets and to said probes, for the detection in the plasma (P), in step b), of atomic and ionic emission lines of sulfur and iodine, respectively, in order to lift the indeterminate nature of the signals generated both by these probes and by these targets.

27. The method as claimed in claim 26, wherein the following are detected in step (b):
chlorine emission lines at a wavelength with a value chosen from the group consisting of 35±3 nm, 386±3 nm, 413±3 nm, 479±3 nm, 490±3 nm, 499±3 nm, 507±3 nm, 521±3 nm, 539±3 nm, 542±3 nm, 774±3 nm, 725±3 nm, 741±3 nm, 754±3 nm, 822±3 nm, 833±3 nm, 837±3 nm, 842±3 nm, 858±3 nm, 868±3 nm, 894±3 nm, 912±3 nm, 919±3 nm, 928±3 nm, 945±3 nm and 959±3 nm; or else
bromine emission lines at a wavelength with a value chosen from the group consisting of 154±3 nm, 158±3 nm, 163±3 nm, 614±3 nm, 635±3 nm, 655±3 nm, 663±3 nm, 751±3 nm, 780±3 nm, 793±3 nm, 798±3 nm, 813±3 nm, 827±3 nm, 844±3 nm, 889±3 nm, 916±3 nm and 926±3 nm.

28. The method as claimed in claim 14, wherein DNA is used for said targets and in that a cation bound to these targets and chosen from the group consisting of sodium, magnesium and potassium is used as element to be quantified, for the detection in the plasma, in step b), of phosphorus, atomic and ionic emission lines.

29. The method as claimed in claim 28, wherein the following are detected in step (b):
sodium emission lines at a wavelength with a value chosen from the group consisting of 268±3 nm, 285±3 nm, 291±3 nm, 292±3 nm, 298±3 nm, 314±3 nm, 321±3 nm, 325±3 nm, 330±3 nm, 353±3 nm, 363±3 nm, 449±3 nm, 466±3 nm, 497±3 nm, 569±3 nm, 589±3 nm, 616±3 nm and 819±3 nm; or
magnesium emission lines at a wavelength with a value chosen from the group consisting of 285±3 nm, 880±3 nm, 309±3 nm, 333±3 nm, 383±3 nm, 457±3 nm, 473±3 nm, 518±3 nm, 552±3 nm, 571±3 nm, 925±3 nm, 964±3 nm and 941±3 nm; or else
potassium emission lines at a wavelength with a value chosen from the group consisting of 404±3 nm, 535±3 nm, 580±3 nm, 693±3 nm, 766±3 nm, 769±3 nm, 825±3 nm, 850±3 nm, 890±3 nm and 959±3 nm.

30. The method as claimed in claim 16, wherein the nitrogen and/or the carbon and/or the oxygen present in said targets and said probes is (are) used as element(s) to be quantified for the detection in the plasma (P), in step b), of the nitrogen and/or carbon and/or oxygen atomic emission lines for evaluating the amount of targets and of probes on said support (2), which contains neither carbon nor nitrogen nor oxygen.

31. The method as claimed in claim 30, wherein the following are detected in step (b):
nitrogen emission lines at a wavelength with a value which is chosen from the group consisting of 174±3 nm, 575±3 nm, 744±3 nm, 821±3 nm, 859±3 nm, 865±3 nm, 871±3 nm, 938±3 nm and 870±3 nm;
carbon emission lines at a wavelength with a value which is chosen from the group consisting of 156+3 nm, 165±3 nm, 175±3 nm, 193±3 nm, 247±3 nm, 538±3 nm, 600±3 nm, 711±3 nm, 833±3 nm, 908±3 nm, 911±3 nm, 965±3 nm and 940±3 nm; and/or
oxygen emission lines with a wavelength with a value which is chosen from the group consisting of 615±3 nm, 645±3 nm, 700±3 nm, 725±3 nm, 777±3 nm, 822±3 nm, 844±3 nm and 926±3 nm.

32. A device (1) for carrying out a method for high speed quantitative measurement of biomolecular targets as claimed in claim 1 wherein the device comprises:
a biological analysis support (2), on or in which biomolecular targets are present and which defines measuring points,
a plasma generating unit (3) which comprises means (4) for focusing and superimposing, on each measuring point, at least two laser beams (F''') by simultaneous intersection of these beams on this support to extract therefrom a hot plasma (P) containing at least one chemical element to be quantified, which is present in said targets and at least one other chemical element exogenous to the targets and present in a known amount on or in the support, these means for focusing and superimposing the beams comprising a scanning head (7) capable of forming them in a collinear manner and a system of mirrors (11) arranged at the outlet of this head, which comprises optical rotating disks (12 and 13) with mirrors (12a and 13a) to deflect the beams toward the support to scan the measuring points of the support,
means for optical containment (5, 5', 5") of each plasma extracted by this plasma generating unit, which are arranged above this support, and
a spectrography unit which is connected to these containment means by acquisition optical fibers (6, 6', 6") emerging into said containment means, and which is suitable for detecting and analyzing emission light lines from the plasma extracted for each measuring point, such that the concentration of said element(s) to be quantified is determined in each measuring point on the basis of one of the intensities of these lines and on the basis of calibration curves, via a correlation between the intensities of the lines specific to this element to be quantified and the concentrations of this element in mixtures, in known proportions, of the or of each element to be quantified and of the or of each exogenous element.

33. The device (1) as claimed in claim 32, wherein said means (4) for focusing and superimposing, by intersection on said support (2), the laser beams (F''') on each measuring point comprise:
a) said scanning head (7) which comprises:
an upside-down reflecting pyramid (8) comprising at least one stage (8a) configured to tangentially reflect incident beams (F) emitted by several laser sources (9) to make them collinear on leaving this pyramid, and
an afocal optical system (10) which is arranged below the tip of this pyramid, and which is configured to receive these collinear beams (F'), while reducing their respective diameters and the distances separating them from one another, and
b) said system of mirrors (11) which cooperates with said optical rotating disks (12 and 13) with mirrors (12a and 13a) deflecting them in horizontal and vertical directions and which also cooperates with a deviation periscope (14) coupled to these disks so that the collinear beams reduced by this afocal system are focused and intersected on each measuring point.

34. The device (1) as claimed in claim 32, wherein said optical containment means (5, 5', 5") are capable of optically containing each plasma (P) extracted and comprise a plurality of open chambers which are each delimited by a sidewall (5a, 5b, 5c, 5a') arranged perpendicularly to said support (2), the inner face of this wall being capable of reflecting the light accumulated in this chamber and at least one of said acquisition optical fibers (6, 6', 6") passing through this wall.

35. The device (1) as claimed in claim 34, wherein said means for optical containment of each plasma (P) comprise a plurality of adjacent rings (5) for integration of the light emitted by this plasma, said sidewall (5a, 5b, 5c) being substantially circular in cross section, the free end of several of said acquisition fibers (6) emerging inside the chamber formed by each ring via orifices (5d) made in said wall, means for relative movement of these chambers with respect to the support (2), comprising rails for sliding (17) the chambers equipped with electromagnets (18), being provided to cover the entire surface of said support to be analyzed.

36. The device (1) as claimed in claim 34, wherein said means for optical containment of each plasma (P) comprise a plurality of chambers for integration (5') of the light emitted by this plasma, said sidewall (5a') of each chamber having a cross section substantially in the form of an equilateral triangle and these chambers being contiguous in pairs via one of their sides, while being each provided with said acquisition fibers (6') at each of their three vertices, means for relative movement of the chambers with respect to the support (2), comprising rails for sliding (17) said chambers equipped with electromagnets (18), being provided to cover the entire surface of said support to be analyzed.

37. The device (1) as claimed in claim 34, wherein said means for optical containment of each plasma (P) comprise a plurality of chambers for integration (5") of the light emitted by this plasma, which are equipped with at least two series of acquisition fibers (6") arranged in staggered rows, the respective optical apertures of which are capable of covering by mutual overlapping (19) the entire surface, of said support (2), to be analyzed without relative movement of these chambers with respect to said support.

38. The device (1) as claimed in claim 32, wherein said chambers for optical containment (5') of the plasmas (P) are themselves housed in a closed enclosure (20) which contains said support (2) and which is filled with a plasmagenic gas, at least the upper face (21) of this enclosure being transparent to the or each excitation wavelength of the laser beams and to the acquisition wavelengths for the light generated by this plasma, this enclosure being equipped with a valve for filling (23) with plasmagenic gas and a valve for flushing of air (22).

39. The device (1) as claimed in claim 32, wherein said spectrography unit comprises at least one spectrograph of photosensitive cell type and in that a diffraction grating or at least one optical filter transparent only to the desired wavelength is arranged between each acquisition optical fiber (6, 6', 6") and said spectrograph.

40. The device (1) as claimed in claim 32, wherein said biological analysis support (2) is formed from a biochip comprising, at its surface, an array of probes which are native, hybridized or complexed by said targets, this array comprising a multitude of said measuring points each comprising a plurality of said probes, and said or each chemical element to be quantified being present in said targets and also in said probes.

* * * * *